(12) United States Patent
Bardsley et al.

(10) Patent No.: US 12,053,403 B2
(45) Date of Patent: Aug. 6, 2024

(54) IMPLANT DELIVERY SYSTEM AND METHOD OF USE

(71) Applicant: SHANGHAI WALLABY MEDICAL TECHNOLOGIES CO., INC., Shanghai (CN)

(72) Inventors: Earl Bardsley, San Clemente, CA (US); Dean Schaefer, Irvine, CA (US); Jerome Choe, Los Angeles, CA (US); Tan Dinh, Santa Ana, CA (US); Luis Cardenas, Moreno Valley, CA (US); Chengcheng Feng, Irvine, CA (US); Cheng Ian, Irvine, CA (US); Paul Dao, Houston, TX (US); Paul Ehlinger, Louisville, KY (US)

(73) Assignee: SHANGHAI WALLABY MEDICAL TECHNOLOGIES CO., INC., Shanghai (CN)

( * ) Notice: Subject to any disclaimer, the term of this patent is extended or adjusted under 35 U.S.C. 154(b) by 586 days.

(21) Appl. No.: 17/259,454

(22) PCT Filed: Jul. 11, 2019

(86) PCT No.: PCT/US2019/041480
§ 371 (c)(1),
(2) Date: Jan. 11, 2021

(87) PCT Pub. No.: WO2020/014536
PCT Pub. Date: Jan. 16, 2020

(65) Prior Publication Data
US 2021/0275337 A1    Sep. 9, 2021

Related U.S. Application Data

(60) Provisional application No. 62/697,383, filed on Jul. 12, 2018.

(51) Int. Cl.
*A61F 2/966* (2013.01)
*A61B 17/12* (2006.01)
(Continued)

(52) U.S. Cl.
CPC .......... *A61F 2/966* (2013.01); *A61B 17/1214* (2013.01); *A61B 2017/00526* (2013.01);
(Continued)

(58) Field of Classification Search
CPC ........ A61B 2017/1205; A61B 17/1214; A61B 2017/00526; A61B 2017/12054;
(Continued)

(56) References Cited

U.S. PATENT DOCUMENTS

| | | |
|---|---|---|
| 5,217,484 A | 6/1993 | Marks |
| 5,312,415 A | 5/1994 | Palermo |

(Continued)

FOREIGN PATENT DOCUMENTS

| | | |
|---|---|---|
| EP | 1582152 B1 | 10/2005 |
| EP | 2190359 B1 | 6/2010 |

(Continued)

*Primary Examiner* — Sarah A Long
*Assistant Examiner* — James R McGinnity
(74) *Attorney, Agent, or Firm* — Helen S Liu (57) ABSTRACT

The present teachings provide a medical system for delivering and deploying a medical implant, and the method of using thereof. Specifically, one aspect of the present teachings provides a medical system having an implant with an engagement loop, and a delivery system having an engagement wire and an engagement mechanism. During implant delivery, the engagement wire engages the engagement loop of the implant. The engagement wire further interacts with the engagement mechanism in order to prevent unintended disengagement of the engagement loop from the engagement wire. The present teaching also provide an implant release mechanism that is configured to break away from the (Continued)

implant pusher shaft. Specially, one aspect of the present teaching provides that the implant release mechanism being of one unit with the implant pusher shaft. To release the implant, a clinician simply breaks away the implant release mechanism from the rest of the implant delivery system.

9 Claims, 6 Drawing Sheets (51) Int. Cl.
  A61B 17/00 (2006.01)
  A61F 2/95 (2013.01)
(52) U.S. Cl.
  CPC .............. *A61B 2017/12054* (2013.01); *A61F 2002/9511* (2013.01)
(58) Field of Classification Search
  CPC ........ A61B 17/3468; A61F 2/95; A61F 2/966; A61F 2002/9511
  See application file for complete search history.

(56) References Cited

U.S. PATENT DOCUMENTS

| | | | |
|---|---|---|---|
| 5,334,199 A * | 8/1994 | Yoon ................ | A61B 17/12013 606/139 |
| 5,582,619 A | 12/1996 | Ken | |
| 5,833,705 A | 11/1998 | Ken et al. | |
| 5,853,418 A | 12/1998 | Ken et al. | |
| 6,013,084 A | 1/2000 | Ken et al. | |
| 6,193,728 B1 | 2/2001 | Ken et al. | |
| 6,936,058 B2 | 8/2005 | Forde et al. | |
| 7,166,122 B2 | 1/2007 | Aganon et al. | |
| 7,367,987 B2 | 5/2008 | Balgobin et al. | |
| 7,371,251 B2 | 5/2008 | Mitelberg et al. | |
| 7,371,252 B2 | 5/2008 | Balgobin et al. | |
| 7,377,932 B2 | 5/2008 | Mitelberg et al. | |
| 7,422,569 B2 | 9/2008 | Wilson et al. | |
| 7,485,122 B2 | 2/2009 | Teoh | |
| 7,572,246 B2 | 8/2009 | Wilson et al. | |
| 7,608,058 B2 | 10/2009 | Wilson et al. | |
| 7,695,484 B2 | 4/2010 | Wallace et al. | |
| 7,708,754 B2 | 5/2010 | Balgobin et al. | |
| 7,708,755 B2 | 5/2010 | Davis, III et al. | |
| 7,766,933 B2 | 8/2010 | Davis, III et al. | |
| 7,799,052 B2 | 9/2010 | Balgobin et al. | |
| 7,811,305 B2 | 10/2010 | Balgobin et al. | |
| 7,819,891 B2 | 10/2010 | Balgobin et al. | |
| 7,819,892 B2 | 10/2010 | Balgobin et al. | |
| 7,883,526 B2 | 2/2011 | Jones et al. | |
| 7,901,444 B2 | 3/2011 | Slazas | |
| 7,927,348 B2 | 4/2011 | Jones et al. | |
| 7,938,845 B2 | 5/2011 | Aganon et al. | |
| 7,985,238 B2 | 7/2011 | Balgobin et al. | |
| 8,029,464 B2 | 10/2011 | Wilson et al. | |
| 8,029,465 B2 | 10/2011 | Wilson et al. | |
| 8,029,466 B2 | 10/2011 | Wilson et al. | |
| 8,029,467 B2 | 10/2011 | Wilson et al. | |
| 8,157,852 B2 | 4/2012 | Bloom et al. | |
| 8,162,971 B2 | 4/2012 | Wilson et al. | |
| 8,167,838 B2 | 5/2012 | Wilson et al. | |
| 8,167,839 B2 | 5/2012 | Wilson et al. | |
| 8,172,862 B2 | 5/2012 | Wallace et al. | |
| 8,177,746 B2 | 5/2012 | Wilson et al. | |
| 8,211,141 B2 | 7/2012 | Davis, III et al. | |
| 8,366,665 B2 | 2/2013 | Wilson et al. | |
| 8,376,995 B2 | 2/2013 | Wilson et al. | |
| 8,376,996 B2 | 2/2013 | Wilson et al. | |
| 8,409,139 B2 | 4/2013 | Wilson et al. | |
| 8,425,461 B2 | 4/2013 | Wilson et al. | |
| 8,439,871 B2 | 5/2013 | Wilson et al. | |
| 8,523,811 B2 | 9/2013 | Wilson et al. | |
| 8,535,345 B2 | 9/2013 | Desai et al. | |
| 8,540,671 B2 | 9/2013 | Wilson et al. | |
| 8,608,772 B2 | 12/2013 | Wilson et al. | |
| 8,821,441 B2 | 9/2014 | Wilson et al. | |
| 8,888,806 B2 | 11/2014 | Desai et al. | |
| 8,926,650 B2 | 1/2015 | Que et al. | |
| 9,089,333 B2 | 7/2015 | Wilson et al. | |
| 9,101,361 B2 | 8/2015 | Wilson et al. | |
| 9,204,882 B2 | 12/2015 | Wilson et al. | |
| 9,307,999 B2 | 4/2016 | Li et al. | |
| 9,339,275 B2 | 5/2016 | Trommeter et al. | |
| 9,358,021 B2 | 6/2016 | Losordo et al. | |
| 9,375,333 B1 | 6/2016 | Aboytes et al. | |
| 9,439,661 B2 | 9/2016 | Johnson et al. | |
| 9,480,479 B2 | 11/2016 | Chen et al. | |
| 9,486,223 B2 | 11/2016 | Que et al. | |
| 9,918,718 B2 | 3/2018 | Lorenzo | |
| 10,045,765 B2 | 8/2018 | Rafiee et al. | |
| 10,052,108 B2 | 8/2018 | Aguilar et al. | |
| 10,098,657 B2 | 10/2018 | Losordo et al. | |
| 10,111,682 B2 | 10/2018 | Johnson et al. | |
| 10,182,822 B2 | 1/2019 | Freudenthal | |
| 10,206,685 B2 | 2/2019 | Trommeter et al. | |
| 2003/0032757 A1 | 2/2003 | Lin | |
| 2003/0172436 A1 | 9/2003 | Thompson | |
| 2003/0211493 A1 | 11/2003 | Baughn et al. | |
| 2004/0002732 A1 | 1/2004 | Teoh et al. | |
| 2004/0006354 A1 | 1/2004 | Schaefer et al. | |
| 2004/0006363 A1 | 1/2004 | Schaefer | |
| 2006/0050884 A1 | 3/2006 | O'Brien | |
| 2006/0116708 A1 | 6/2006 | Ogawa et al. | |
| 2006/0116714 A1 | 6/2006 | Sepetka et al. | |
| 2006/0276825 A1 | 12/2006 | Mitelberg et al. | |
| 2006/0276826 A1 | 12/2006 | Mitelberg et al. | |
| 2006/0276827 A1 | 12/2006 | Mitelberg et al. | |
| 2006/0276830 A1 | 12/2006 | Balgobin et al. | |
| 2006/0276833 A1 | 12/2006 | Balgobin et al. | |
| 2007/0239193 A1 | 10/2007 | Simon et al. | |
| 2008/0097462 A1 | 4/2008 | Mitelberg et al. | |
| 2008/0306503 A1 | 12/2008 | Que et al. | |
| 2010/0137898 A1 | 6/2010 | Teoh | |
| 2011/0092997 A1 | 4/2011 | Kang | |
| 2011/0213406 A1 | 9/2011 | Aganon et al. | |
| 2012/0041472 A1 * | 2/2012 | Tan .................. | A61B 17/12113 606/200 |
| 2012/0116441 A1 | 5/2012 | Yamanaka et al. | |
| 2012/0179194 A1 | 7/2012 | Wilson et al. | |
| 2012/0197289 A1 | 8/2012 | Wilson et al. | |
| 2012/0253381 A1 | 10/2012 | Forsythe et al. | |
| 2013/0138141 A1 | 5/2013 | Wilson et al. | |
| 2013/0138142 A1 | 5/2013 | Wilson et al. | |
| 2013/0325054 A1 | 12/2013 | Watson | |
| 2014/0277341 A1 | 9/2014 | Havel et al. | |
| 2014/0330299 A1 | 11/2014 | Rosenbluth et al. | |
| 2015/0157329 A1 * | 6/2015 | Rudakov .......... | A61B 17/12031 606/198 |
| 2016/0228124 A1 | 8/2016 | Trommeter et al. | |
| 2017/0245865 A1 | 8/2017 | Jones et al. | |
| 2018/0161038 A1 | 6/2018 | Lorenzo | |
| 2018/0228494 A1 | 8/2018 | Walzman | |
| 2018/0303486 A1 | 10/2018 | Rosenbluth et al. | |
| 2018/0317924 A1 | 11/2018 | Aguilar et al. | |
| 2019/0021755 A1 | 1/2019 | Johnson et al. | |

FOREIGN PATENT DOCUMENTS

| | | | |
|---|---|---|---|
| EP | 2422716 A1 | 2/2012 | |
| EP | 2674114 A1 | 12/2012 | |
| EP | 2668914 A1 | 12/2013 | |
| WO | WO200754118 A1 | 5/2007 | |
| WO | WO2015148821 A1 | 1/2015 | |
| WO | WO-2018022186 A1 * | 2/2018 | ....... A61B 17/12113 |
| WO | WO201851187 A1 | 3/2018 | |
| WO | WO201853314 A1 | 4/2018 | |
| WO | WO2018210907 A1 | 11/2018 | |

* cited by examiner

IMPLANT DELIVERY SYSTEM AND METHOD OF USE

CROSS-REFERENCE TO RELATED APPLICATION

This application is a U.S. national phase application under 37 U.S.C. § 371 of International Application No. PCT/US2019/041480 filed on Jul. 11, 2019, which claims priority to and the benefit of U.S. Provisional Patent Application Ser. No. 62/697,383, entitled "Implant Delivery System and Method Of Use," filed Jul. 12, 2018. The entirety of each of PCT/US2019/041480 and U.S. Provisional Application Ser. No. 62/697,383 are incorporated herein by reference.

TECHNICAL FIELD

The present invention relates generally to systems and method for delivery of one or more implants into a patient, and in particular implant delivery systems and devices that provide a rapid release of the implant at a desired implantation location.

BACKGROUND OF THE INVENTION

Vaso-occlusive devices, stents and other implants are used for a variety of medical treatments, including the treatment of intra-vascular aneurysms and vascular restrictions. Vaso-occlusive devices often include a soft, helically wound coil that is positioned in a blood vessel or aneurysm, such as a blood vessel or aneurysm of the brain. Stents can comprise resiliently biased structures that self-expand or plastically deformable structures that are expanded through the use of an inflatable balloon. Vaso-occlusive devices, stents and other implants are often accompanied by a catheter-based delivery device which is introduced percutaneously into a patient, and advanced proximate a site for implantation. Precision of placement of one or more implants at a desired location is often difficult to the manner in which the implant is released from the delivery catheter.

SUMMARY

An aspect of the present teachings provides an implant delivery system for delivering and deploying an implant into a patient. The delivery system comprises an implant pusher shaft, an implant engagement feature, an implant release mechanism and an implant engagement wire. The implant pusher shaft comprises a proximal end, a distal end, and a longitudinal lumen. The implant pusher shaft also has a distal flexible portion, a middle transition portion, and a proximal portion, wherein the implant pusher shaft. The implant engagement feature has a cylindrical body joining to the distal end of the implant pusher shaft, two fingers extending distally from the cylindrical body, and a cross pin joining the two fingers. The implant release mechanism releasably attaches to the proximal end of the implant pusher shaft. The implant engagement wire slidably disposes within the longitudinal lumen of the implant pusher shaft. The implant engagement wire having a distal end and a proximal end. The proximal end of the implant engagement wire joins the implant release mechanism.

One embodiment of the present teachings provides that the implant delivery system comprises an implant delivery configuration and an implant release configuration. In the implant delivery configuration, the implant release mechanism attaches to the implant pusher shaft and the distal end of the implant engagement wire extends distally beyond the cross pin of the implant engagement feature. In the implant release configuration, the implant release mechanism detaches from the implant pusher shaft and the distal end of the implant engagement wire retracts proximally back inside the longitudinal lumen of the implant pusher shaft.

One embodiment of the present teachings provides that the implant release mechanism is of one unity with the implant pusher shaft with a circumferentially weakened location in between. In another embodiment of the present teachings, the implant release mechanism is configured to break away from the implant pusher shaft at the circumferentially weakened location.

One embodiment of the present teachings provides that the flexible portion of the implant pusher shaft has a first stiffness; and the proximal portion of the implant pusher shaft has a second stiffness. The second stiffness is greater than the first stiffness. Another embodiment of the present teachings provides that the transition portion of the implant pusher shaft is configured with a gradual increasing stiffness from the first stiffness at a distal end to the second stiffness at a proximal end.

One embodiment of the present teachings provides that the flexible portion of the implant pusher shaft comprises a multi-filar tube.

One embodiment of the present teachings provides that the transition portion of the implant pusher shaft comprises an inner liner having a longitudinal lumen and a hypotube extending over the inner liner and an outer jacket. The hypotube of the transition portion has a laser cutting pattern with more material remove at its distal portion than its proximal portion.

One embodiment of the present teachings provides that an inner liner forming the longitudinal lumen of the implant pusher shaft extends from the proximal portion to the flexible portion of the of the implant pusher shaft.

One embodiment of the present teachings provide that a hypo tube extends from the proximal portion to the transition portion of the of the implant pusher shaft. The hypo tube extends over the inner liner that forms the longitudinal lumen of the implant pusher shaft. Another embodiment of the present teachings provide that at least a portion of the hypo tube at the transition portion of the implant pusher has less stiffness than at least a portion of the hypo tube at the proximal portion of the implant pusher shaft.

One embodiment of the present teachings provide that a medical system for delivering and deploying an implant into a patient. The medical system comprises a medical implant and an implant delivery system. The medical implant has an engagement loop configured to releasably engaging to an implant delivery system. The implant delivery system comprises an implant engagement feature and an implant engagement wire. The implant engagement feature has two fingers extending distally at a distal end of the implant delivery system. A cross pin joins the two fingers. The implant engagement wire slidably disposes within a longitudinal lumen of the implant delivery system.

One embodiment of the present teachings provide that as the implant delivery system engages the medical implant, the engagement loop extends proximally over the cross pin from a first side; the implant engagement wire extends distally first through the engagement loop of the medical implant first, then further distally over the cross pin from a second side, and thereby trapping the engagement loop.

One embodiment of the present teachings provide that the medical system has a first configuration where the medical implant engages to the implant delivery system, and a second configuration where the medical implant disengages from the implant delivery system. When in its second configuration, the proximal end of the engagement wire extends proximally away from the cross pin and releases the engagement loop of the medical implant.

One embodiment of the present teachings provide that the medical implant has a coil body with an axial lumen and a stretch resistance member joining the coil body at a distal end of the coil body. A distal end of the engagement loop joins a proximal end of the stretch resistance member.

One embodiment of the present teachings provide that the engagement loop is configured to be extended proximally and longitudinally outside of a proximal end of the coil body in a tensioned state. One embodiment of the present teachings provide that the engagement loop is made of superelastic material.

An aspect of the present teachings provides a medical implant comprising a coil body (102), a stepper band, a stretch resistance member, and an engagement loop joining a proximal end of the stretch resistance member by an anchor band. The coil body includes an axial lumen. The stepper band has an axial lumen, and joins a proximal end of the coil body. The stretch resistance member joins a distal end of the coil body, and extends inside the axial lumen of the coil body. The engagement loop extends through the axial lumen of the stepper band and the axial lumen of the coil body. In one embodiment of the present teaching, the anchor band has a greater exterior profile than axial lumen of the stepper band such that when the anchor band engages the stepper band, an interference between the anchor band and the stepper band is then formed. In one embodiment, the engagement loop releasably engages to an implant delivery system.

DETAILED DESCRIPTION

Certain specific details are set forth in the following description and figures to provide an understanding of various embodiments of the present teachings. Those of ordinary skill in the relevant art would understand that they can practice other embodiments of the present teachings without one or more of the details described herein. Thus, it is not the intention of the applicant(s) to restrict or in any way limit the scope of the appended claims to such details. While various processes are described with reference to steps and sequences in the following disclosure, the steps and sequences of steps should not be taken as required to practice all embodiments of the present teachings.

As used herein, the term "lumen" means a canal, a duct, or a generally tubular space or cavity in the body of a subject, including a vein, an artery, a blood vessel, a capillary, an intestine, and the like. The term "lumen" can also refer to a tubular space in a catheter, a sheath, a hollow needle, a tube, or the like.

As used herein, the term "proximal" shall mean close to the operator (less into the body) and "distal" shall mean away from the operator (further into the body). In positioning a medical device inside a patient, "distal" refers to the direction relatively away from a catheter insertion location and "proximal" refers to the direction relatively close to the insertion location.

As used herein, the term "wire" can be a strand, a cord, a fiber, a yarn, a filament, a cable, a thread, or the like, and these terms may be used interchangeably.

As used herein, the term "sheath" may also be described as a "catheter" and, thus, these terms can be used interchangeably.

Unless otherwise specified, all numbers expressing quantities, measurements, and other properties or parameters used in the specification and claims are to be understood as being modified in all instances by the term "about." Accordingly, unless otherwise indicated, it should be understood that the numerical parameters set forth in the following specification and appended claims are approximations. At the very least and not as an attempt to limit the application of the doctrine of equivalents to the scope of the claims, numerical parameters should be read in light of the number of reported significant digits and the application of ordinary rounding techniques.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third etc. may be used herein to describe various limitations, elements, components, regions, layers and/or sections, these limitations, elements, components, regions, layers and/or sections should not be limited by these terms.

These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between," "adjacent" versus "directly adjacent," etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

Spatially relative terms, such as "beneath," "below," "lower," "above," "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The terms "reduce", "reducing", "reduction" and the like, where used herein, are to include a reduction in a quantity, including a reduction to zero. Reducing the likelihood of an occurrence shall include prevention of the occurrence.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

The term "diameter" where used herein to describe a non-circular geometry is to be taken as the diameter of a hypothetical circle approximating the geometry being described. For example, when describing a cross section, such as the cross section of a component, the term "diameter" shall be taken to represent the diameter of a hypothetical circle with the same cross sectional area as the cross section of the component being described.

The terms "major axis" and "minor axis" of a component where used herein are the length and diameter, respectively, of the smallest volume hypothetical cylinder which can completely surround the component.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

The present teaching relate to an implant-delivery system assembly for engaging, delivering, deploying and releasing one or more implants into a patient. In some embodiment, the delivery system includes an implant pusher shaft for pushing the implant forward during delivery and deployment; an implant engagement mechanism configured to releasably engage a medical implant during delivery and deployment. The delivery system further includes an implant release mechanism for disengaging the medical implant and release it at the treatment location. The control mechanism is constructed and arranged to release the engagement between the implant and the delivery system.

Figure 1:
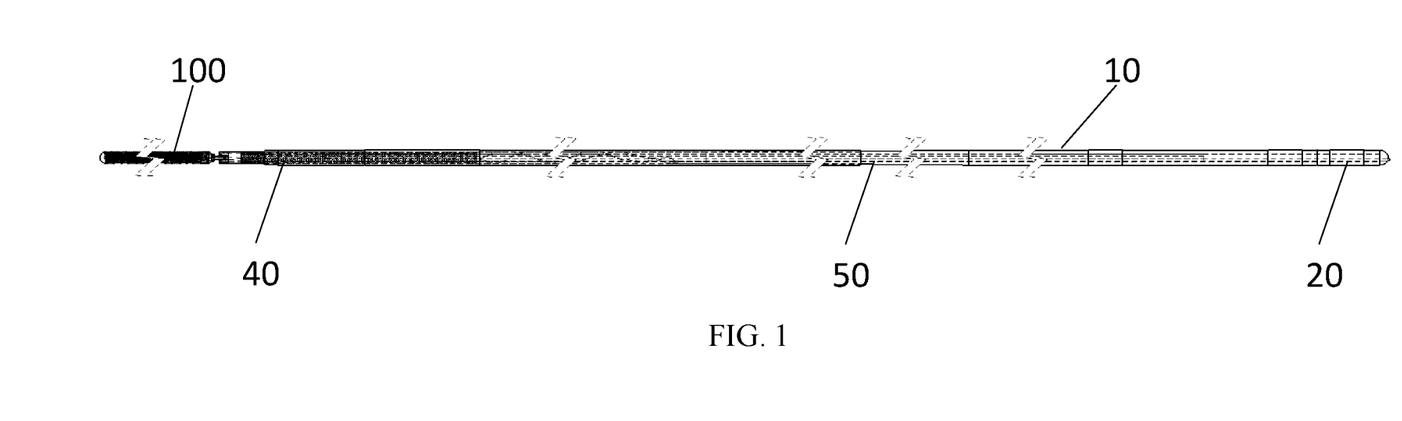
FIG. 1 is a perspective view of a medical system where an implant engages to an implant delivery system in accordance with the present teachings.

FIG. 1 illustrates an embodiment of an implant (100) engaging to a delivery system (10). During implant delivery, as shown in this figure, a proximal end of the implant (100) engages a distal end of the delivery system (10). The delivery system (10), according to some embodiments, includes an implant release mechanism (20), an implant pusher shaft (50), and an implant engagement wire (40). The implant release mechanism (20) is at a proximal end of the implant pusher shaft (50), and is configured to be broken away from the implant pusher shaft (50). A proximal end of the implant engagement wire (40) fixedly attaches to the implant release mechanism (20). As shown in FIG. 1, during implant delivery, the implant release mechanism (20) attaches to the proximal end of the implant pusher shaft (50). And the delivery system (10) engages the implant by the pusher shaft (50) and the implant engagement wire (40).

Figure 2:
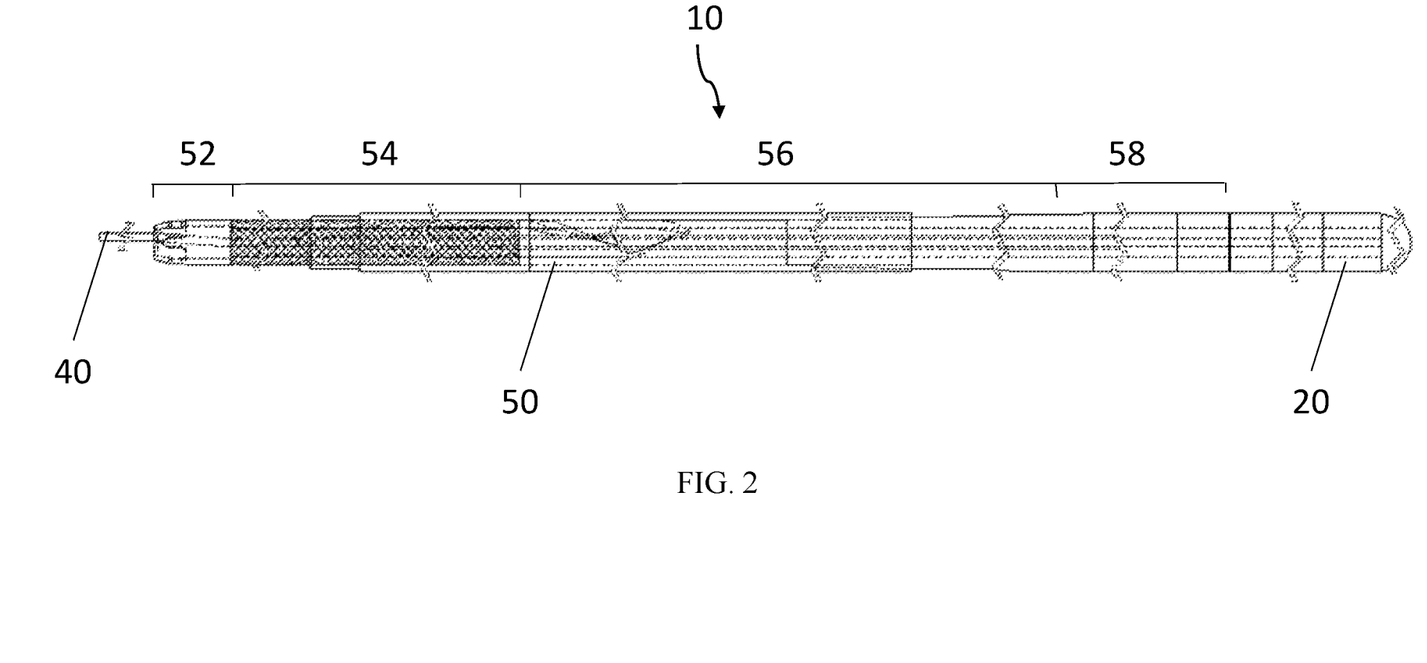
FIG. 2 is a perspective view of an exemplary implant delivery system in accordance with the present teachings.

Now referring to FIG. 2, according to one embodiment of the present teaching, the implant pusher shaft (50) has a proximal end, a distal end, and a longitudinal lumen extending from the proximal end to its distal end. According to one embodiment, the implant pusher shaft (50) is configured to have a gradual decreased stiffness from its proximal end to its distal end. In another word, the stiffness of the implant pusher shaft (50) is designed to gradually increase from its distal end to its proximal end. The relative less stiff distal portion is configured to minimize the impact to the surround vessel tissue as the implant pusher shaft (50) being extended toward the treatment location. The relative stiff proximal portion (58) is configured to provide adequate force to advance the implant (100). According one embodiment, the implant pusher shaft (50) includes a distal flexible portion (54) with a distal end attaching to an implant engagement feature (52), a middle transition portion (56), and a proximal portion (58). Without attempting to limit the scope of present teachings, the distal flexible portion (54) of the implant pusher shaft (50) is configured to offer mechanical properties such as column strength for pushing the medical implant (100), stretch resistance when the product is retracted, and flexibility when the distal end of the implant pusher shaft (50) enters the aneurysm or when the medical implant (100) is deployed.

Figure 3A:
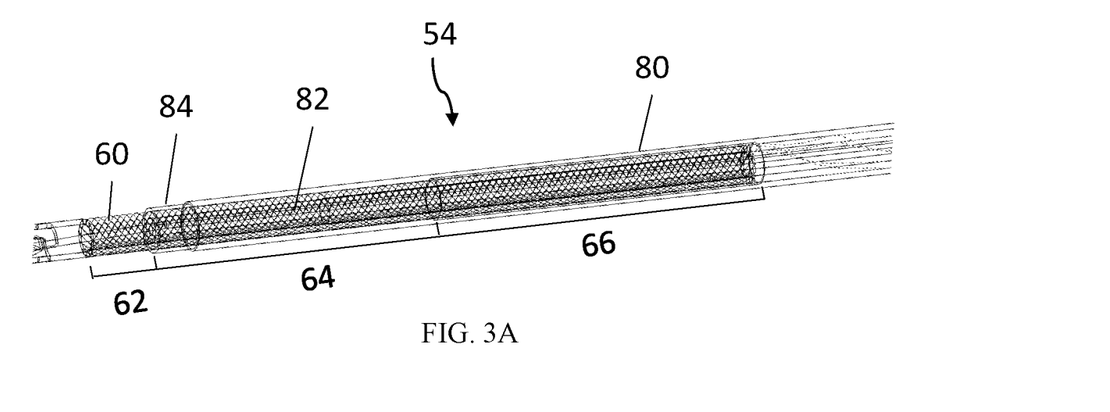
FIG. 3A is a perspective view of a distal flexible portion of an exemplary implant pusher shaft in accordance with the present teachings.
Figure 3B:
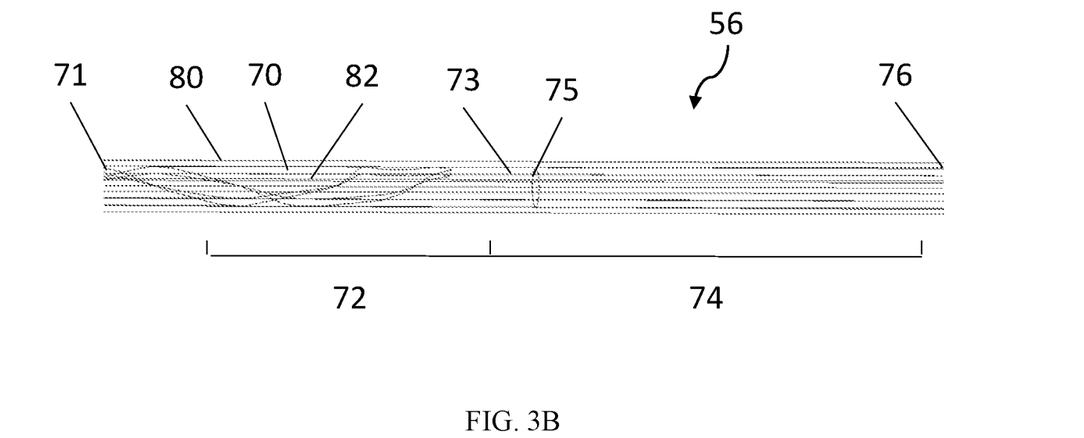
FIG. 3B is a perspective view of a middle transition portion of an exemplary implant pusher shaft in accordance with the present teachings.

As illustrated in the FIG. 3A, the flexible portion (54) of the implant pusher shaft (50) is constructed to have a gradual increase in its stiffness from its proximal end to its distal end. This design purpose is achieved by construct different layers at various sections of the flexible portion (54). As illustrated in FIG. 3B, the transition portion (56) of the implant pusher shaft (50) is constructed of a hypotube (70) extending over an inner liner (82). The hypotube (70) at distal portion of transition portion (56) has a reduced outer profile/diameter and a spiral cutting pattern. The hypotube (70) at proximal portion (74) of transition portion (56) has a tapered outer profile with a gradual increase in its outer diameter toward the proximal end of the transition portion (56). An outer jacket (80) extends over the distal portion (72) of the transition portion (56). As illustrated in the FIG. 3C, the proximal portion (58) of the implant pusher shaft (50) is constructed of a hypotube (70) without any cutting pattern alone over an inner liner (82). According to one embodiment, the hypotube (70) in the proximal portion (58) of the implant pusher shaft (50) has a constant profile, similar to the outer diameter at the proximal end of the transition portion (56).

According to one embodiment, as illustrated in FIG. 2 and FIGS. 3A-3C, the inner liner (82) has an elongated lumen extending from a middle section (64) of the flexible portion (54) to a place near the proximal end of the proximal portion (58) of the implant pusher shaft (50). According to one embodiment, the inner liner (82) has a 0.004" inner diameter and a 0.006" outer diameter. The outer jacket (80) extends from a middle section (64) of the flexible portion (54) to the proximal end of the distal portion (72) of the transition portion (56) of the implant pusher shaft (50). The hypotube (70), with various outer diameter and cutting pattern, extends from the transition portion (56) to the proximal portion (58) of the implant pusher shaft (50). According to one embodiment, the hypotube (70) has a 0.007" inner diameter. In one embodiment, the outer jacket (80) is configured to provide a lubricious surface and added column strength as well as stretch resistance to the implant pusher shaft (50).

Thus, as disclosed in the present teaching, the distal portion (54) of the implant pusher shaft (50) is more flexible than the middle portion (56) of the implant pusher shaft (50); and the middle portion (56) of the implant pusher shaft (50) is more flexible than the proximal portion (58) of the implant pusher shaft (50). In another word, the distal portion (54) of the implant pusher shaft (50) is less stiff than the middle portion (56) of the implant pusher shaft (50); and the middle portion (56) of the implant pusher shaft (50) is less stiff than the proximal portion (58) of the implant pusher shaft (50).

Now referring to FIG. 3A, according to one embodiment, the distal flexible portion (54) of the implant pusher shaft (50) is constructed of a multi-filar tube (60) made with multi wires wounded in a helical configuration forming a longitudinal lumen. According to some embodiments, the multi-filar wire tube (60) comprises 6, 8, 12, or 18 wires. In another embodiment, the multi-filar tube (60) could be wound in a left hand or a right hand direction. In another embodiment, the multi-filar tube (60) could have a closed pitch of 4-8 mm. In yet other embodiments, the filament used in the multi-filar tube (60) construction ranges from 0.001" to 0.003" in size. According to one preferred embodiment of the present teaching, the distal flexible portion (54) of the implant pusher shaft (50) is constructed of an 18-wire multi-filar wire tube wounded in a hand direction, with a pitch of 6.3 mm.

According to one embodiment, the multi-filar tube (60) extends throughout the entire flexible portion (54). A distal section (62) of the flexible portion (54) has multi-filar tube (60) alone. A middle section (64) and a proximal section (66) of the multi-filar tube (60) are lined with an inner liner (82). The middle section (64) of the multi-filar tube (60) further has a shrink tube layer extending in between the inner layer and the multi-filar tube (60). The proximal section (66) of the multi-filar tube (60) further incorporate an additional layer of the shrink tube extending over the exterior luminal surface of the multi-filar tube (60). An outer jacket (80) extends over the middle and proximal sections (64, 66) of the flexible portion (54) to provide additional stiffness and surface smoothness.

Thus, According to one embodiment of the present teaching, a distal section (62) of the flexible portion (54) of the implant pusher shaft (50) has a one-layer construction, i.e. the multi-filar tube (60). A middle section (64) of the flexible portion (54) of the implant pusher shaft (50) has a 4-layer construction, an outer jacket (80) over the multi-filar tube (60) over a shrink tube and finally over an inner liner (82). A proximal section (66) of the flexible portion (54) of the implant pusher shaft (50) has a 5-layer construction, i.e. an outer jacket (80) over a first shrink tube over the multi-filar tube (60) over a shrink tube and finally over an inner liner (82). With this construction, the proximal section (66) of the flexible portion (54) is stiffer than the middle section (64) of the flexible portion (54) of the implant pusher shaft (50). And the middle section (64) of the flexible portion (54) of the implant pusher shaft (50) is stiffer than the distal section (62) of the flexible portion (54) of the implant pusher shaft (50).

One skilled in the art should understand this embodiment of the present teaching provides only one exemplary way to vary the stiffness within the same portion of the implant pusher shaft (50), i.e. by adding additional material layer, such as a shrink tube layer. Thus the specific numbers of the construction layer should only be viewed as a reference, and should not be viewed as limiting to the scope of the present teaching.

Continue referring to FIG. 3A, according to one embodiment of the present teaching, the radiopaque marker band (84) is incorporated at a distal end of the middle section (64), i.e. the 4-layer section, of the flexible portion (54) of the implant pusher shaft (50). According to one embodiment, the marker band (84) has a 0.0131" outer diameter and a 0.0115" inner diameter and a 2-3 mm length.

According to one embodiment of the present teaching, the flexible portion (54) of the implant pusher shaft (50) is about 30 cm long, with its distal 1-layer construct section (62) about 2-3 cm long, its middle 4-layer construct section (64) about 10-15 cm long, and its proximal 5-layer construct section (66) about 13-17 cm. According to one embodiment, the multi-filar tube (60) has a 0.011"-0.0145" outer diameter and a 0.007"-0.0085" inner diameter. One skilled in the art should understand that overall length and size of the flexible portion (54) of the implant pusher shaft (50) could be easily modified to fit for a specific application. Thus, the specific number disclosed herein should be considered as a reference, and should not be viewed as limiting to the scope of the claim.

Now referring to FIG. 3B, according to one embodiment, the middle transition portion (56) of the implant pusher shaft (50) is constructed of a hypotube (70) extending over an inner liner (82). According to one embodiment, a distal section (62) of the hypotube (70) has a reduced outer diameter with a laser cutting pattern. The outer jacket (80), extends over the laser cutting pattern in order to provide a smoother exterior. A proximal section (66) of the hypotube (70) has a gradual tapered outer profile with a reduced diameter distal end (75) and a larger diameter at its proximal end (76).

According to one embodiment, the distal section (62) of the transition portion (56) of the implant pusher shaft (50) is configured to have a gradual increase in flexibility from its distal portion to its proximal portion (58). In another word, the distal section (62) of the transition portion (56) of the implant pusher shaft (50) is configured to have a gradual decrease in stiffness from its distal section (72) to its proximal section (74). To achieve this purpose, in one embodiment, the hypotube (70) in the distal section (72) of the transition portion (56) of the implant pusher shaft (50) has some material removed, i.e. by a laser cutting pattern. The more material removed, the more flexible, and the less stiff, the hypotube (70) is. Thus, to achieve a gradual decrease in flexibility and increase in stiffness, the amount of material removed gradually decreases from its distal end (71) to its proximal end (73). According to one embodiment of the present teaching, the laser cutting pattern is in a helical shape with the pitch of the helix decreased from a distal end (71) to a proximal end (73) of the distal section (72) of the transition portion (56). One skilled in the art should understand that other material removing manner could also be incorporated here. For example, the thickness of the hypotube (70) could gradually increase from its distal section (72) to its proximal section (74). In another example, the material removing could be the result of another pattern, and/or in combination with the change in thickness of the hypotube (70).

According to one embodiment, the proximal section (74) of the transition portion (56) of the implant pusher shaft (50) is configured to have a gradual increase in flexibility from its distal end (75) to its proximal end (76). In another word, the proximal section (74) of the transition portion (56) of the implant pusher shaft (50) is configured to have a gradual decrease in stiffness from its distal end (75) to its proximal end (76). To achieve this purpose, in one embodiment, the hypotube (70) in the proximal section (74) of the transition portion (56) of the implant pusher shaft (50) has a gradual change in its wall thickness. According to one embodiment, as the inner diameter of the hypotube (70) remains consistent throughout the transition (56) and proximal portion (58) of the implant pusher shaft (50), the outer diameter of the hypotube (70) in the distal section (74) of the transition portion (56) of the implant pusher shaft (50) is grinded down to a smaller diameter, thereby reduce the wall thickness of the hypotube (70) in this section. The outer profile of the proximal section (74) of the transition portion (56) of the implant pusher shaft (50) is then grinded to a tapered shape with a smaller diameter matching the distal section 72) and a larger dimeter matching the proximal portion (58) of the implant pusher shaft (50). Thus, the wall thickness of the hypotube (70) in this section gradually increased toward the proximal portion (58).

Continue referring to FIG. 3B, the transition portion (56) further comprises an inner liner (82) extends throughout this portion. In one embodiment, the distal end of the hypotube (70) in the transition is welded to the proximal end of the multi-filar tube (60) of the flexible portion (54) of the implant pusher shaft (50). The transition portion (56) further comprises an outer jacket (80) extending over the distal section (62) of the transition portion (56). In one embodiment, the outer jacket (80) is configured to provide a smooth external surface of the hypotube (70), as well as increase the stiffness of the transition portion (56). According to one embodiment of the present teaching, the hypotube (70) in the transition portion (56) of the implant pusher shaft (50) is a continuous piece with the hypotube (70) in the proximal portion (58) of the implant pusher shaft (50). In another embodiment, the outer jacket (80) in the transition portion (56) of the implant pusher shaft (50) is a continuous piece with the outer jacket (80) in the flexible portion (54) of the implant pusher shaft (50). In one embodiment, the distal end (71) of the transition portion (56) has a similar flexibility and/or stiffness to the proximal section (66) of the flexible portion (54) of the implant pusher shaft (50). In another embodiment, the proximal end (76) of the transition portion (56) has a similar flexibility and/or stiffness to the proximal portion (58) of the implant pusher shaft (50).

According to one embodiment of the present teaching, the transition portion (56) of the implant pusher shaft (50) is about 28-37 cm long with the distal section (72) of the transition portion (56) about 10-15 cm long, and proximal section (74) of the transition portion (56) about 18-22 cm long. The distal section (62) of the transition portion (56) has an outer diameter about 0.011". The proximal section (66) of the transition portion (56)'s outer diameter gradually increases from 0.01" to 0.014". One skilled in the art should understand that overall length and size of the transition portion (56) of the pusher shaft could be easily modified to fit for specific application. Thus, the number disclosed herein should be considered as a reference, and should not be viewed as limiting to the scope of the invention.

Figure 3C:
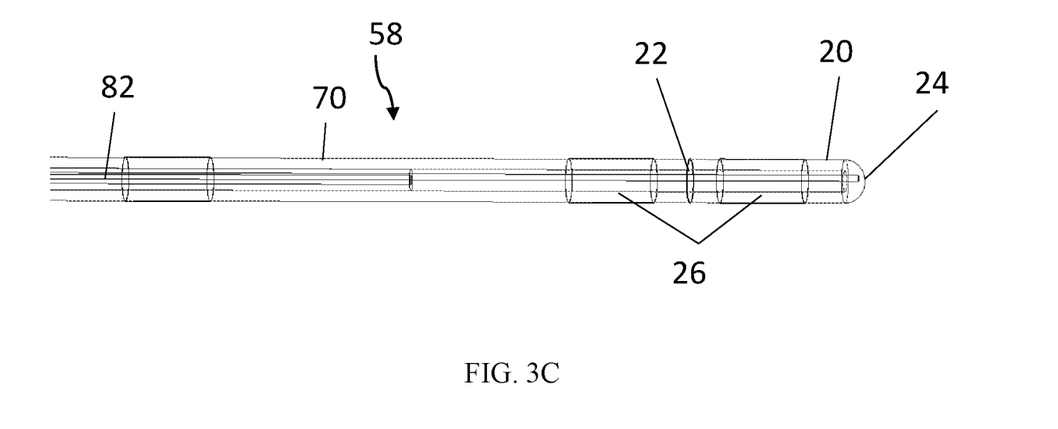
FIG. 3C is a perspective view of a proximal portion of an exemplary implant pusher shaft in accordance with the present teachings.

Now referring to FIG. 3C, according to one embodiment, the proximal portion (58) of the implant pusher shaft (50) is constructed of a hypotube (70) extending over an inner liner (82). Unlike the transition portion (56), the proximal portion (58) of the hypotube (70) of the proximal portion (58) of the implant pusher shaft (50) is a solid tube has no material removed, and thus with a consistent stiffness throughout its length. According to one embodiment of the present teaching, the proximal end of the inner liner (82) locates proximal to the proximal end of the hypotube (70).

According to one embodiment of the present teaching, the proximal portion (58) of the implant pusher shaft (50) is about 120 cm long, with an inner diameter of 0.007" and an outer diameter of 0.014". In another embodiment of the present teaching, the proximal end of the inner liner (82) is 12-20 mm away from the proximal end of the hypotube (70). One skilled in the art should understand that overall length and size of the proximal portion (58) of the pusher shaft could be easily modified to fit for specific application. Thus, the number disclosed herein should be considered as a reference, and should not be viewed as limiting to the scope of the claim.

One skilled in the art should also understand that in order to achieve desired variable in flexibility and/or stiffness in the implant pusher shaft (50), other technique could be incorporated. For example, the flexible portion (54) can be constructed of a unifilar tube, multi-filar tube (60), or a braid. In some embodiments, the tube construct can be of a helical or spiral pattern. In another embodiments, the transition portion (56) could also be constructed in a coil configuration with a gradual increase in the stiffness. In one embodiment, multi-filar tube (60) in the flexible portion (54) and the hypotube (70) in both the transition (56) and proximal portion (58) are the same material. In another embodiment, the multi-filar tube (60) in the flexible portion (54) and the hypotube (70) in both the transition and proximal portion (58) are different material. In one embodiment, the multi-filar tube (60) in the flexible portion (54) and the hypotube (70) in both transition (56) and proximal portion (58) are one continuous piece with difference construction. In another embodiment, as described with reference to FIGS. 3A-3B, the multi-filar in the flexible portion (54) and the hypotube (70) in both transition (56) and proximal portion (58) are two separate pieced which are joined together by the inner liner (82).

In another embodiment of the present teaching, in order to achieve desired variable in flexibility and/or stiffness in the implant pusher shaft (50), the overall size of implant pusher shaft (50) could varies from portion to portion. For example, the implant pusher shaft (50) could have a tapered transition portion (56) with a smaller size at its distal end, a greater size at its proximal end, and a smooth transition in between. The overall size of the flexible portion (54) is similar to the size of the distal end (71) of the transition portion (56), and the overall size of the proximal portion (58) is similar to the size of the proximal end (76) of the transition portion (56). For example, the proximal portion (58) of the implant pusher shaft (50) could have a 0.014" general diameter, and the flexible portion (54) of the implant pusher shaft (50) could have a 0.011" general diameter.

In some embodiments, the implant pusher shaft (50) is made of one or more plastic and/or metal materials, each independently chosen from stainless steels; shaped memory metals; nickel titanium alloys; polymers; shaped memory polymers; or combinations of one or more of these. In other embodiments, the filament used in making the coil/braid construction can be of a metal and/or a plastic.

In one embodiment, the outer jacket (80) is made of a polymer, for example PTFE or PET which is a heat shrinkable material, or a combination of both. In another embodiment, the outer jacket (80) has a thickness between 0.0010" and 0.0025". In yet another embodiment, the outer jacket (80) could have various thickness covering each portion of the implant pusher shaft (50). Although an outer jacket (80) is disclosed and described here, one skilled in the art should understand that as the design, material, and/or construct of the implant pusher shaft (50) varies, the outer jacket (80) might not be necessary. Thus, what has been disclosed herein should not be viewed as limiting to the overall scope of the present teachings.

Referring back to FIG. 2, the proximal end of the implant pusher shaft (50) joins to an implant release mechanism (20). According to one embodiment of the present teaching, the implant release mechanism (20) is configured to attach to the implant pusher shaft (50) during implant delivery and break away from the implant pusher shaft (50) in order to release the implant (100).

Figure 4:
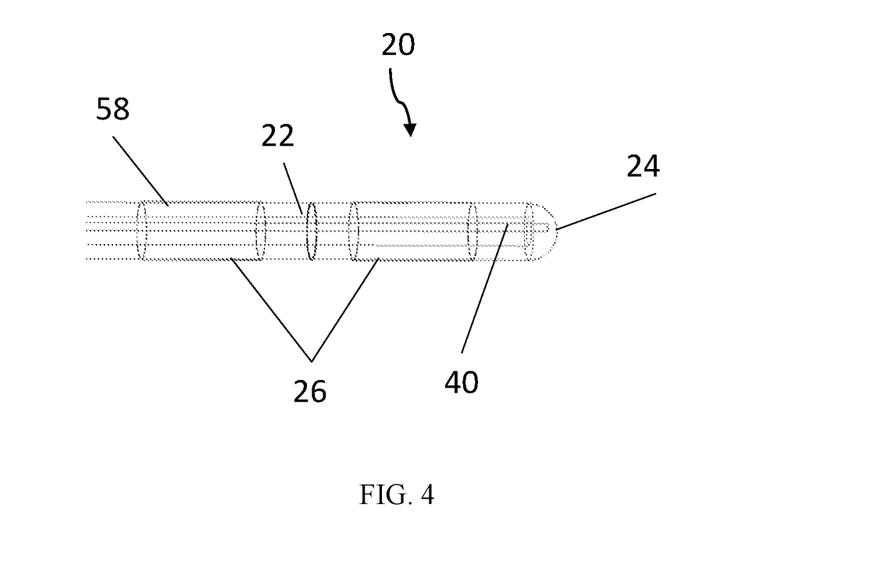
FIG. 4 is a perspective view of an exemplary implant release mechanism attaching to an implant engagement wire in accordance with the present teachings.

Now referring to FIG. 4, according to one embodiment of the present teaching, the implant release mechanism (20) is of one piece construction with the proximal portion (58) of the implant pusher shaft (50). Specifically, in one embodiment, the implant release mechanism (20) is has a tubular body made of the same hypotube (70) extending beyond the proximal end of the implant pusher shaft (50). In between the implant pusher shaft (50) and the implant release mechanism (20) has a circumferentially weakened spot (22). In one embodiment, the circumferentially weakened location is achieved by various means known to those skilled in the art such as reducing the thickness of the outer jacket (80), removing material, or perforating material along the circumference of the hypotube (70). One skilled in the art should understand that other technique could also have been used to achieve the circumferentially weakened location. According to one embodiment of the present teaching, to release the implant (100), a clinician bends the implant release mechanism (20) to an angle, resulting a break-away of hypotube (70) of the implant release mechanism (20) from the proximal portion (58) of the implant pusher shaft (50).

According to one embodiment, the implant release mechanism (20) has a longitudinal lumen extending from its distal end to its proximal end. At the proximal end of the implant release mechanism (20), a cap (24) is used to joins the proximal end of the implant engagement wire (40) to the proximal end of the implant release mechanism (20). The cap (24) is also configured to close the proximal end of the hypotube (70) of the implant release mechanism (20).

According to one embodiment of the present teaching, the implant release mechanism (20) has an overall length of 45-55 mm, an overall size similar to the proximal portion (58) of the implant pusher shaft (50).

Continue referring to FIG. 4, two shrink bands (26) have been incorporated, one on the implant release mechanism (20), proximal to the circumferentially weakened spot (22) between the implant release mechanism (20) and the implant pusher shaft (50), the other one on the proximal portion (58) of the implant pusher shaft (50) distal to the circumferentially weakened spot (22). In one embodiment, the shrink bands (26) is to indicate clinician a holding location for a clean break-away of the implant release mechanism (20) from the implant pusher shaft (50). Thus, in one embodiment, the shrink bands (26) is configured to have a different color than the outer jacket (80) of the implant pusher shaft (50). In another embodiment, the shrink bands (26) is configured to have a different surface feature than the outer jacket (80) of the implant pusher shaft (50). In one embodiment, both shrink bands (26) are 19 mm away from the circumferentially weakened spot (22). In another embodiment, both shrink bands (26) are 25 mm in length.

Referring back to FIG. 2, an implant engagement wire (40) slidably disposes within the axial lumen of the implant pusher shaft (50) and the implant release mechanism (20). According to one embodiment of present teachings, the implant engagement wire (40) is configured to extend distally or retract proximally independent of the implant pusher shaft (50). A proximal end of the implant engagement wire (40) fixes to the proximal end of the implant release mechanism (20).

Now referring to FIG. 4, in one embodiment, the proximal end of the implant engagement wire (40) extends through the axial lumen of the implant release mechanism (20) and fixedly joins to the proximal end of the implant release mechanism (20). According to one embodiment, the proximal end of the implant engagement wire (40) joins to the implant release mechanism (20) through a chemical mean (for example, an adhesive), a thermal mean (for example, welding), or a mechanical means (for example, crimping). In one exemplary embodiment, an epoxy cap is used to fuse the proximal end of the implant engagement wire (40) to the proximal end of the implant pusher shaft (50). One skilled in the art should understand, the above described epoxy cap is only one exemplary embodiment for such attachment, other techniques known in the field could all be incorporated to achieve the same purpose According to one embodiment, as a clinician breaks away the implant release mechanism (20), the implant engagement wire (40) retracts proximally relative to the implant pusher shaft (50). As explained herein, this configuration prevents the implant engagement wire (40) from accidentally extending distally during implant delivery. Thus, as the implant pusher shaft (50) remains steady, the implant engagement wire (40) can only be retracted proximally independent of the implant pusher shaft (50) when breaking the engagement between the implant pusher shaft (50) and the implant release mechanism (20). Without limiting the scope of the present teachings with any particular theory, such a design would prevent an accidental advancement of the implant and avoid any damage to nearby anatomy.

In some embodiments, the implant engagement wire (40) can be made of a metal and/or a plastic material, each chosen from stainless steels, superelastic metals, nickel titanium alloys, shaped memory alloys, shaped memory polymers, polymers, or combinations of one or more of the foregoing. In some embodiments, the implant engagement wire (40) has a general diameter between 0.001" and 0.005". In other embodiments, a proximal portion (58) and/or a distal portion of the implant engagement wire (40) has a different physical property or is made of a different material.

Now referring back to FIG. 2, the distal end of the implant pusher shaft (50) joins to an implant engagement feature (52). The implant engagement feature (52) fixedly joins to the distal end of the implant pusher shaft (50) and is configured to engage the implant with the implant engagement wire (40).

Figure 5:
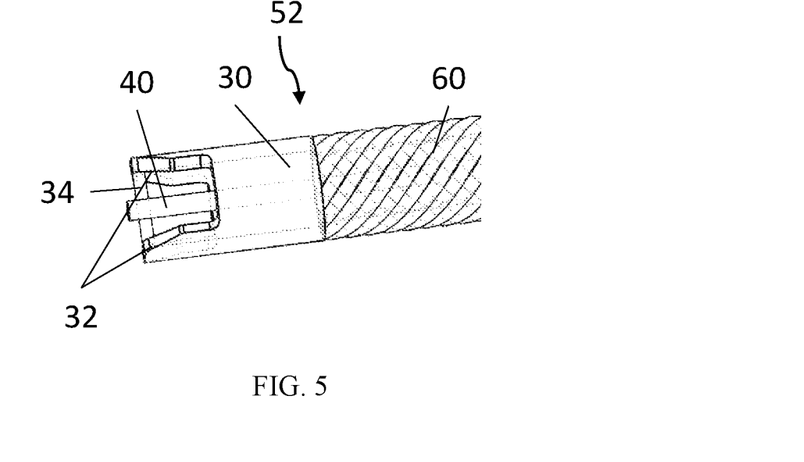
FIG. 5 is a perspective view of an exemplary implant engagement feature in accordance with the present teachings.

Now referring to FIG. 5, according to one embodiment of the present teaching, the implant engagement feature (52) has a cylindrical body portion (30) with an axial lumen connected to the distal end of the multi-filar tube (60), two fingers (32) extending distally from the cylindrical body portion (30), an a cross pin (34) joining two opposing fingers (32). Although FIG. 5 illustrates that the two fingers (32) as directly opposing each other across the axial center of the implant pusher shaft (50), one skilled in the art should understand that modifications could be made according to the treatment purpose and location, such as the two fingers (32) could be configured to be not directly across each other from the axial center. Additionally, FIG. 5 illustrates that the cross pin (34) joins two fingers (32) at their distal tips, and one skilled in the art should understand that the location where the cross pin (34) joins the fingers can vary according to the need during the manufacturing process. Thus, the specific embodiments disclosed herein should not be viewed as limiting to the scope of the present teachings.

Figure 6:
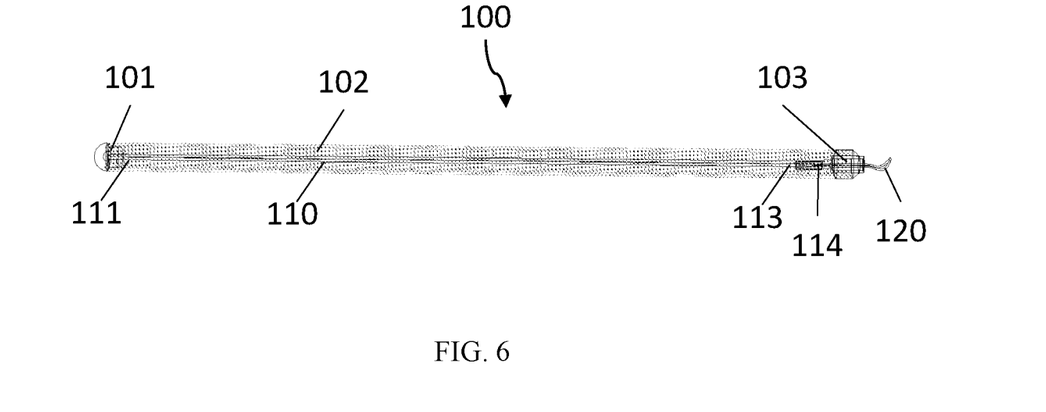
FIG. 6 is a perspective view of an implant in accordance with the present teachings.

According to some embodiments, the overall length of the implant engagement feature (52) is about 0.5 mm with the two fingers (32) ranging from 0.008" to 0.04". The overall size of the axial lumen of the implant engagement feature (52) is configured to be similar to the overall size of the axial lumen of the multi-filar tube (60). According to one embodiment, the cross pin (34) has a diameter around 0.001" to 0.002". According to some embodiment, the different part of the implant engagement feature (52) is made of different material. In one embodiment, the cross pin (34) is made of stainless steel, the fingers (32) are made of platinum or iridium Now referring to FIG. 6, one exemplar embodiment of the coil implant (100) is shown in its elongated delivery profile, according to one embodiment of the present teaching. As illustrated, the implant (100) has a coil body (102) extending from a proximal end (103) to a distal end (101), with an elongated lumen extended from one end to the other end of the coil body (102). The implant (100) further includes a stretch resistance member (110), and an engagement loop (120), where the proximal end (113) of the stretch resistance member (110) and the distal lend (122) of the engagement loop (120) are joined together by an anchor band (114). Both the stretch resistance member (110) and the engagement loop (120) extend inside the axial lumen of the coil boy (102).

Figure 7A:
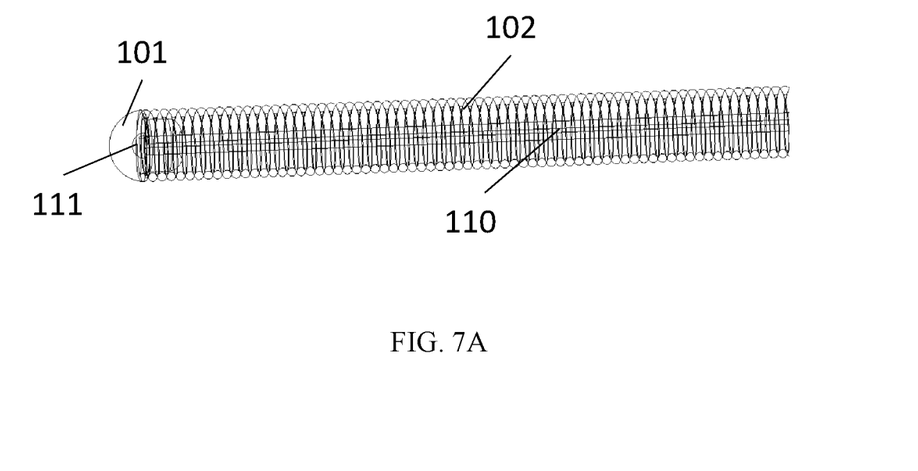
FIG. 7A is a perspective view of a distal portion of the exemplary implant engagement feature in accordance with the present teachings.

FIG. 7A illustrates a distal end portion of the implant (100). In one embodiment, the stretch resistance member (110) is made of polypropylene and/or another plastic material. The distal end (111) of the stretch resistance member (110) joins the distal end (101) of the coil body (102). For example, as shown in FIG. 7A, the distal end (111) of the stretch resistance member (110) has an enlarged distal end with a smaller ball and a distal cap, all in one piece. The distal cap is configured to be positioned outside and against the distal end the coil body (102) with the smaller ball positioned inside the coil lumen. In one embodiment, the enlarged distal end of the stretch resistance member (110) could be of the same material as the rest portion of the member, for example, polypropylene and/or another plastic material. In another embodiment, the enlarged distal end of the stretch resistance member (110) could be made of a radiopaque material or is incorporated with a radiopaque material. In one embodiment, epoxy is used to fuse the enlarged distal end of the stretch resistance member (110) to the distal end (101) of the coil body (102). According to one embodiment, such enlarged distal end of the stretch resistance member (110) is configured to increase the tensile value. When pulling on the resistance member (110), the tensile force is transferred to the distal cap and subsequently onto the coil body (102). This configuration prevents accidental detachment between the distal end (111) of the stretch resistance member (110) from the distal end (101) of the coil body (102). One skilled in the art should understand, the above described technique is only one exemplary embodiment for such attachment, other techniques known in the field could all be incorporated to achieve the same purpose. For example, the distal end (111) of the stretch resistance member (110) could join to the distal end (101) of the coil body (102) by any chemical means (for example, an adhesive), any thermal means (for example, welding), or any mechanical means (for example, friction) known to those skilled in the field.

According to one embodiment, the coil body (102) of the implant (100) is made of platinum tungsten alloy, platinum, or platinum iridium alloy. It overall length in the delivery profile is 1 cm to 60 cm. The coil body (102) is configured to have none or minimum stretchability. One skilled in the art should understand that if the coil body (102) is stretched, a physician will have to employ a greater amount of force in order to retrieve implant (100) back into the delivery system (10). In one embodiment, the coil body (102) is a continuous coil, or a plurality of coils that connect with one another. In one embodiment, each coil body (102) is made of platinum, platinum tungsten alloy, and platinum iridium alloy. In one embodiment, the coil body (102) could have an outer diameter of 0.009"-0.018". In a preferred embodiment, the coil body (102) has an outer diameter of 0.011"-0.015".

According to one embodiment, the stretch resistance member (110) is made of polypropylene or other suitable plastic material. In one embodiment, the stretch resistance member (110) has a general size of 0.0008" to 0.0035" in diameter. In a preferred embodiment, the stretch resistance member (110) has a general size of 0.001" to 0.002" in diameter. The stretch resistance member (110) is configured to resist stretch in order to minimize the tension on the coil body (102). According to one embodiment, the stretch resistance member (110) has an overall length general similar to the length of the coil body (102). Thus, during implant deliver, the proximal end of the stretch resistance member (110) rests within the axial lumen of the coil body (102).

Figure 7B:
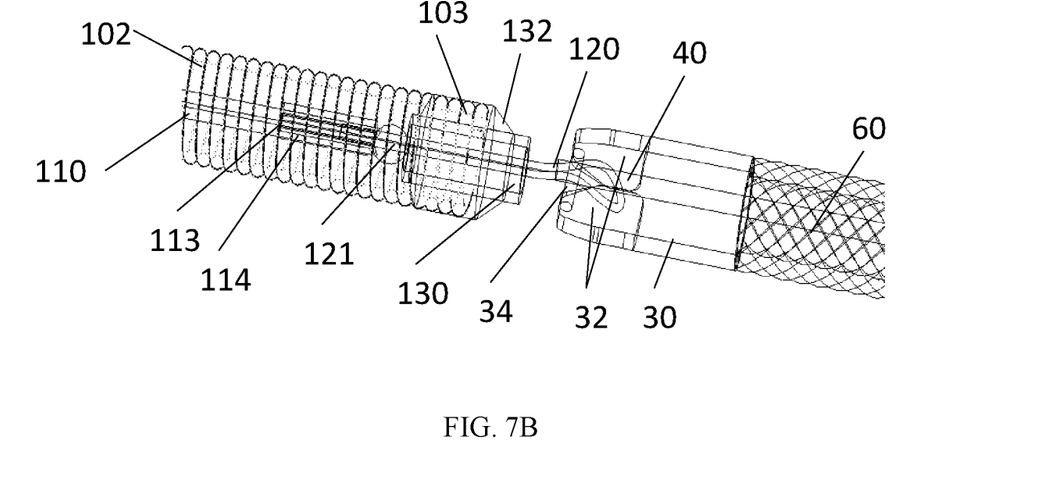
FIG. 7B is a perspective view of a proximal portion of the exemplary implant engagement feature in accordance with the present teachings.

FIG. 7B illustrates a proximal end portion of the implant (100) as the implant engaging to the delivery system (10). According to one embodiment of the present teaching, the proximal end (113) of the stretch resistance member (110) joins to a distal end (121) of an engagement loop (120) by an anchor band (114). As shown in the figure, the anchor band (114) crimps both free ends (121) of the engagement loop (120) to a proximal end (113) of the stretch resistance member (110). According to one exemplary embodiment, the proximal end (113) of the stretch resistance member (110) is in a form of a knot, preventing it accidentally slipping through the anchor band (114). In one embodiment, the anchor band (114) has an overall length of 0.012". One skilled art should understand that other technique could be used to join the stretch resistance member (110) to the engagement loop (120). Thus what has been disclosed above should only be considered as one exemplary embodiment, and should not be used to limit the scope of the present teaching.

Continue referring to FIG. 7B, the proximal end (103) of the coil body (102) engages to a stepper band (130). As shown in the figure, the stepper band (130) has a cylindrical body with an axial lumen configured to extend partially inside the axial lumen of the coil body (102). According to one embodiment, a distal portion of the stepper band (130) extends from the proximal end into the axial lumen of the coil body (102). A proximal portion (58) of the stepper band (130) remains outside and proximal to the coil body (102). According to one embodiment, the stepper band (130) joins to the coil body (102) by frictional fit. In another embodiment, as shown in FIG. 7B, epoxy is used to fuse the stepper band (130) to the coil body (102). As shown in the figure, epoxy (132) binds the proximal end of the coil boy with the stepper bank, and forms a proximal ramp toward the end of the epoxy binding. According to one embodiment, this ramp is configured to help the re-entry of coil body (102) back into a delivery sheath. One skilled in the art should understand that although epoxy is used to join the stepper band (130) to the coil body (102), weld, or other methods known in the field could also be used In one embodiment, the stepper band (130) has an outer diameter of 0.0065" and an overall length of 0.0125"-0.016" with ⅔ length housed inside the axial lumen of the coil body (102), and ⅓ length remains outside. The stepper band (130) further includes a through lumen of 0.0075" in diameter. The through lumen of the stepper band (130) is configured to allow the engagement loop (120) to extend through. In one embodiment, the stepper band (130) is made of platinum iridium alloy material. In another embodiment, stepper band (130) works to transfer pushing force applied by the cross pin (34) to the entire coil body (102).

According to one embodiment of the present teaching, the anchor band (114) is configured to have a slightly greater outer profile than the inner diameter of the stepper band (130). Thus, when implant (100) is pulled proximally, the anchor band (114) is then being pulling against the stepper band (130). The interference between the anchor band (114) and the stepper band (130) allows the force to be distributed among the entire coil body (102) and the stretch resistance member (110), instead of the stretch resistance member (110) alone. According to one embodiment, the stepper band (130) has an outer diameter of 0.0065"-0.0075", an inner diameter of 0.0045", and an overall length of 0.0125"-0.016". The anchor band (114) has an outer diameter of 0.005", an inner diameter of 0.003" and an overall length of 0.012".

According to one embodiment, the engagement loop (120) is made of filament is a single filar, for example, a polypropylene fiber with a diameter of approximately 0.001" folded into a loop with both open ends crimped to the stretch resistance member (110). In another embodiment, the engagement loop (120) is made of multiple filaments, such as two or more filaments in a side-by-side configuration. In one embodiment, the engagement loop (120) is made of a plastic or metal material, for example a nickel titanium alloy. In another embodiment, the engagement loop (120) is made of material with superelasticity, which facilitates de-attachment between the implant (100) and the implant engagement feature (52). The engagement loop (120) has a general natural length of 1 mm in its collapsed and elongated profile. In one embodiment, the engagement loop could be made of stretchy material allows the loop to be stretched longer from its natural length. As shown FIG. 7B, as the implant (100) engages to the delivery system (10), the engagement loop (120) is stretched so that the loop's proximal end extends beyond the proximal end of the stepper band (130).

FIG. 7B further illustrates an embodiment of the present teaching where the implant (100) engages the delivery system (10). As shown in the figure, the engagement loop (120) is tensioned and therefore extends proximally beyond the proximal end of the stepper band (130) and beyond the cross pin (34) of the delivery system (10). The distal end of the implant engagement wire (40) extends first through the engagement loop (120) of the implant (100), then beyond the cross pin (34) of the implant engagement feature (52), and further distally into the axial lumen of the stepper band (130). As shown in FIG. 7B, engagement loop (120) extends over one side of the cross pin (34), and the engagement wire extends over the opposing side of the cross pin (34), such that the cross pin (34) is secured in between the engagement loop (120) and engagement wire. As the implant engagement wire (40) remains steady, the distal movement of the engagement loop (120) is stopped by the cross pin (34). This allows the implant (100) to be securely engaged to the delivery system (10).

According to one embodiment, during the implant delivery and deployment, as the clinician advances the delivery system (10) distally, the implant (100) is pushed distally, for example, by cross pin (34) pushing onto the proximal end of the stepper band (130). In addition, the engagement between the delivery system (10) and the implant (100) also allows a rotational movement of the delivery system (10) to be transferred to the implant (100).

For illustration purpose, FIG. 7B shows a gap between the cross pin (34) of the delivery system (10) and the proximal end of the stepper band (130) of the implant (100), those skilled in the art should understand that during the implant's distal advancement, there could be no gap. What's shown in FIG. 7B is a merely an illustration solely for the purpose of explaining various embodiments of the present teachings.

As described above, the engagement loop (120) extends proximally over one side of the cross pin (34), and the implant engagement wire (40) extends distally through the center of the engagement loop (120) and over another side of the cross pin (34). In order for the engagement loop (120) to hoop over the cross pin (34), as shown in FIG. 7B, the engagement loop (120) bends away from the longitudinal axis of the implant pusher shaft (50). One skilled in the art should understand that any degree could be possible as long as an attachment is achieved between the delivery system (10) and the coil implant (100). In some embodiment, the distal portion of the engagement wire could be bent to a degree while the engagement loop (120) remain its general linear profile.

Figure 8A:
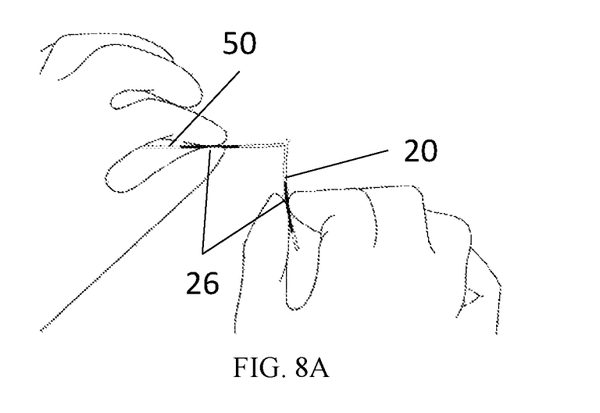
FIG. 8A is a perspective view of the implant release mechanism breaking away from the implant pusher shaft in accordance with the present teachings.
Figure 8B:
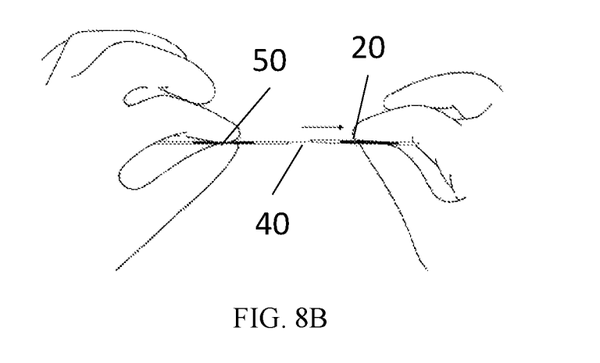
FIG. 8B is a perspective view of the implant engagement wire releasing the engagement loop of the implant in accordance with the present teachings.
Figure 8C:
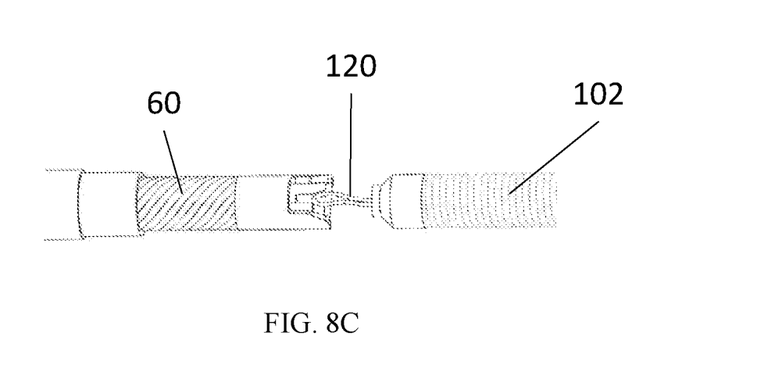
FIG. 8C is a perspective view of the implant release mechanism in accordance with the present teachings.

Once a clinician is satisfied with the positioning and deployment of the coil implant (100), he/she can start the implant releasement process. To release the implant (100), as illustrated in FIG. 8A the clinical first breaks the attachment between the implant release mechanism (20) and the proximal portion (58) of the implant pusher shaft (50) at the pre-fabricated circumferentially weakened spot (22). Once the implant release mechanism (20) breaks away, the clinician then pulls the engagement wire slightly proximal to ensure the detachment of the implant (100) from the implant the delivery system (10). As a result, the distal end portion of the implant engagement wire (40) retracts proximally over the cross pin (34), out of the engagement loop (120), and then back inside the elongated lumen of the implant pusher shaft (50). As a result, the engagement loop (120) of the implant (100) is free from constrain as shown in FIG. 8B. Once freed, the engagement loop (120) relaxes and resume its original non-tensioned profile, and subsequently retracts into the axial lumen of the stepper band (130) or coil body (102).

When deployed at treatment location, the implant (100) relaxes from its general linear delivery profile as it contains inside the delivery sheath, and resumes a pre-configured or randomly-arranged curl profile which fills space at the implantation (such as aneurysm) site. In one embodiment, the stretch resistance member (110) and the engagement loop (120) are configured to be flexible and conforming without imposing any stiffness to the surrounding coil body (102).

Although not specifically described in above description, one skilled in the art should understand that additional access devices could also be used during a treatment procedure. For example, a vascular introducer sheath, such as an introducer sheath comprising high-density polyethylene (HDPE), PTFE, and/or polypropylene can be used for creating a conduit for advancing the delivery system and coil implant assembly to a treatment location. Access devices can also include one or more standard guide catheters, interventional guidewires, and/or microcatheters. A delivery and deployment describe above, although what has been described herein is a coil implant, one skilled in the art should understand that the inventive principle disclosed herein could also apply to other medical implant such as a vaso-occlusive device, a stent and another drug delivery implant.

Although not specifically described in above disclosure, one skilled in the art should understand that a clinician may also employ other tools during a treatment procedure. For example, imaging devices such as fluoroscope; X-ray; CT scanner; MRI; ultrasound imager; and combinations of these could be used during delivery and positioning. In another embodiment, one or more radioopaque markers are used to aid visualization. Such marker could be incorporated either on the medical implant or the delivery system. Without attempting to limit to any particular function, these radioopaque markers can be visualized by using radiographic imaging equipment such as X-ray, magnetic resonance, ultrasound or other imaging techniques. Marker as disclosed herein can be applied to any part of a device or a delivery system of the present teachings. A radioopaque marker can be sewed, adhered, swaged riveted, otherwise placed, and secured in or on the device. The radioopaque marker may be made of tantalum, tungsten, platinum, iridium, gold, or alloys of these materials or other materials that are known to those skilled in the art. The radioopaque marker can also be made of numerous paramagnetic materials, including one or more elements with atomic numbers 21-29, 42, 44, and 58-70, such as chromium (III), manganese (II), iron (III), iron (II), cobalt (II), copper (II), nickel (II), praesodymium (III), neodymium (III), samarium (III), ytterbium (III), gadolinium (III), terbium (III), dysprosium (III), holmium (III) and erbium (III), or other MR visible materials that are known to those skilled in the arts.

One skilled in the art should understand, although most exemplary embodiments described above refers to an embolic coil implant, exemplary embodiments for implant-delivery system attachment embodiments and for the implant release mechanism could be used with other implants such as other vaso-occlusive devices, stents, and etc. In some embodiments, exemplary embodiment for delivery system is constructed and arranged to precisely deliver an implant into an aneurysm, such as a brain aneurysm. In another embodiments, the exemplary embodiment for delivery system is arranged to precisely delivery an implant into a blood vessel such as a blood vessel of the brain, a patent blood vessel, or other locations.

The foregoing description and accompanying drawings set forth a number of examples of representative embodiments at the present time. Various modifications and alternative designs will become apparent to those skilled in the art in light of the foregoing teachings without departing from the spirit hereof, or exceeding the scope hereof, which is indicated by the following claims rather than by the foregoing description. All changes and variations that fall within the meaning and range of equivalency of the claims are to be embraced within their scope.

We claim:

1. An implant delivery system for delivering and deploying an implant into a patient, the delivery system comprising:
    an implant pusher shaft having a distal end, a proximal end, a longitudinal lumen extending from the distal end to the proximal end, and an implant engagement feature at the distal end of the implant pusher shaft, wherein the implant engagement feature comprises two fingers extending distally and a cross pin joining the two fingers;
    an implant release mechanism fixed to the proximal end of the implant pusher shaft; and
    an implant engagement wire slidably disposed within the longitudinal lumen of the implant pusher shaft, wherein the implant engagement wire comprises a distal end and a proximal end;
    wherein as the implant release mechanism fixedly joins the proximal end of the implant pusher shaft, the distal end of the implant engagement wire extends distally beyond the cross pin of the implant engagement feature, and as the implant release mechanism breaks away from the proximal end of the implant pusher shaft, the distal end of the implant engagement wire withdraws proximally away from the cross pin of the implant engagement feature.

2. The implant delivery system of claim 1, wherein the implant release mechanism and at least a proximal portion of the implant pusher shaft are made of one piece hypotube, with a circumferentially weakened location in between.

3. The implant delivery system of claim 2, wherein the circumferentially weakened location is achieved by removing material at said circumferential weakened location.

4. The implant delivery system of claim 3, wherein the circumferentially weakened location has a reduced thickness.

5. The implant delivery system of claim 3, wherein the circumferentially weakened location has a perforating pattern.

6. The implant delivery system of claim 1, wherein at least a portion of the implant pusher shaft comprises an inner liner, a hypotube, and an outer jacket, wherein the hypotube has a helix cutting pattern with a pitch of the helix cutting pattern decreasing from a distal end of the at least a portion of the implant pusher shaft to a proximal end of the at least a portion of the implant pusher shaft.

7. The implant delivery system of claim 1, wherein the implant pusher shaft comprises a distal flexible portion, a middle transition portion, and a proximal portion.

8. The implant delivery system of claim 7, wherein the distal flexible portion is configured with a gradual increasing stiffness from a distal end of the distal flexible portion to a proximal end of the distal flexible portion.

9. The implant delivery system of claim 7, wherein the middle transition portion of the implant pusher shaft is configured with a gradual increasing stiffness from a distal end of the middle transition portion to a proximal end of the middle transition portion.

\* \* \* \* \*